(12) United States Patent
Wang et al.

(10) Patent No.: US 9,097,665 B2
(45) Date of Patent: Aug. 4, 2015

(54) METHOD AND DEVICE FOR ANALYSIS AND READING

(75) Inventors: Jihua Wang, Guangzhou (CN); Zhicai Wang, Guangzhou (CN)

(73) Assignee: Guangzhou Wondfo Biotech. Co., Ltd. (CN)

( * ) Notice: Subject to any disclaimer, the term of this patent is extended or adjusted under 35 U.S.C. 154(b) by 49 days.

(21) Appl. No.: 13/702,468

(22) PCT Filed: Aug. 26, 2011

(86) PCT No.: PCT/CN2011/078967
§ 371 (c)(1),
(2), (4) Date: Dec. 6, 2012

(87) PCT Pub. No.: WO2013/020307
PCT Pub. Date: Feb. 14, 2013

(65) Prior Publication Data
US 2013/0183199 A1  Jul. 18, 2013

(30) Foreign Application Priority Data

Aug. 5, 2011  (CN) .......................... 2011 1 0223580

(51) Int. Cl.
G01N 21/00     (2006.01)
G01N 21/76     (2006.01)
G01N 21/55     (2014.01)
G01N 21/84     (2006.01)

(52) U.S. Cl.
CPC ............ G01N 21/55 (2013.01); G01N 21/8483 (2013.01)

(58) Field of Classification Search
CPC ........................... G01N 21/55; G01N 21/8483

USPC ...................................................... 422/82.05
See application file for complete search history.

(56) References Cited

U.S. PATENT DOCUMENTS 5,580,794 A    12/1996 Allen
5,605,837 A *   2/1997 Karimi et al. ................... 436/14
(Continued)

FOREIGN PATENT DOCUMENTS

CN    1420350 A    5/2003
CN    1573316 A    2/2005
(Continued)

Primary Examiner — Jill Warden
Assistant Examiner — Brittany Fisher
(74) Attorney, Agent, or Firm — Lerner, David, Littenberg, Krumholz & Mentlik, LLP

(57) ABSTRACT

An analyzing and reading device and an analyzing and reading method, for reading and analyzing a test strip for assay detection are disclosed. The test strip has a detection zone and a blank zone, the device includes a photoelectric detection circuit and a processor, wherein the photoelectric detection circuit includes at least two light sources which locate corresponding to the positions of the detection zone and the blank zone of the test strip and are able to emit lights corresponding to the detection zone and blank zone of the test strip, and at least one optical detectors which receive reflected lights from the above two zones; wherein lights emitted by the at least two light sources irradiate the detection zone and blank zone of the strip and are reflected therefrom, and then are received by the optical detector, which in turn feedback the detection information to the processor; the processor making analysis and decision based on the detection information received. The analyzing and reading device and method according to the present invention have high accuracy and less interference when reading.

14 Claims, 3 Drawing Sheets

(56) References Cited

U.S. PATENT DOCUMENTS

| | | | |
|---|---|---|---|
| 5,837,546 A | 11/1998 | Allen et al. | |
| 6,964,752 B2* | 11/2005 | Lappe et al. | 422/82 |
| 2002/0031839 A1* | 3/2002 | McNeirney et al. | 436/518 |
| 2008/0006762 A1* | 1/2008 | Fadell et al. | 250/201.1 |
| 2008/0151539 A1* | 6/2008 | Lee et al. | 362/231 |

FOREIGN PATENT DOCUMENTS

| | | |
|---|---|---|
| CN | 201210144 Y | 3/2009 |
| CN | 1573315 B | 1/2011 |
| CN | 202189015 U | 4/2012 |
| EP | 0291194 A1 | 11/1988 |
| EP | 0653625 A1 | 5/1995 |

* cited by examiner

METHOD AND DEVICE FOR ANALYSIS AND READING

CROSS-REFERENCE OF RELATED APPLICATIONS

The present application is a national phase entry under 35 U.S.C. §371 of International Application No. PCT/CN2011/078967 filed Aug. 26, 2011, which claims priority from Chinese Patent Application No. 201110223580.7, filed Aug. 5, 2011, all of which are incorporated herein by reference.

FIELD OF THE INVENTION

The present invention relates to the field of assay detection, in particular to a method and device for analyzing and reading in assay detection.

BACKGROUND OF THE INVENTION

There have been many devices for analyzing assay substances in the market, and particularly, there are also some related invention patents. For example, EP291194 discloses a cross-flow immunoassay device for testing HCG, which is a single-use test strip that requires a user to interpret the results. However, the interpretation of results has a degree of subjectivity, and a timer should also be provided. On the other hand, the result is displayed by color which will deepen with time and then affect the interpretation of the result. EP653625 discloses a device which gets results by using an optical method; in that device, the test strip disclosed by EP291194 is inserted into a reader, with positioning the strip on an optical element of the reader. The strip is lighted by the light emitted from a light source, and then the reflected or transmitted light will be detected by an optical detector. Typically, the reader includes at least one light-emitting diode (LED), and for each LED, a corresponding optical detector is provided, which belongs to a reusable electronic pen. In a similar analytical device like the above, it is needed to carefully position the analytical reader and the test strip, since a small displacement of a detection or control zone in relation to a corresponding optical detection zone will significantly affect the detector readings due to the quite weak visible signals formed in the detection zone and the control zone. In addition, it is very important that the optical detector must be close to the test strip, because the amount of light captured by a light sensitive diode is very small, and the strength of signal decreases rapidly with the increasing distance from the strip to the detector, for the signal strength usually complies with inverse square law. Thus, the user should carefully position the test stick and the readout of analytical results, particular for a household device. However, for a reusable analytical device, especially for such small-type device, it is easily to cause dislocation by repeated insertions of the strip, while a tiny dislocation will in turn cause an inaccuracy. The replacement of a strip may be result in an improper installation, and then lead to a misjudgment caused by a tiny inaccuracy of the reader which is inherently sensitive to the optical path length.

U.S. Pat. No. 5,837,546 discloses an automatic assay device and method. The device provides an additional electrode by a cross-flow carrier, detects if there is fluid on the carrier, generates a signal to turn on the electronic assay device, and displays the testing result. However, in different tests, the liquid flows along the carrier at different speeds, and different types of flow rate characteristics of liquids will result in inaccuracy readings. Due to the inconsistent characteristics of the materials of the wick and the porous, water-permeable film, the best time for reading will be different.

CN 1573315B discloses a device for reading the analytical results performed by a liquid transporting carrier. This device is directed to solve the problem of how to determine the best reading time, but it cannot solve the problem of different fluids having different flow-rate standards. Meanwhile, for some assay devices, their required detection times are too long, for example, an assay-based, commercial cross-flow detection tool for detecting heart injury takes up to 15 minutes to finish the assay.

CN 1573316B discloses an optical device for assay reading, which also includes a light source and an optical detector, but the device is somewhat complicated and has many more optical paths, thus it is prone to misfortunes which then affect the results. So, the device does not achieve the purpose of optimization.

Therefore, it is necessary to provide a device and method for analysis and reading which have simple detection optical path, less interference, simple structure of detection circuit, and accurate readings.

SUMMARY OF THE INVENTION

An objective of the present invention is to provide an analyzing and reading device with simple structure of detection circuit and accurate readings.

A further objective of the present invention is to provide an analyzing and reading method which is accurate in reading.

To achieve the object of the present invention, the following technical solution is provided:

An analyzing and reading device, for reading and analyzing a test strip for assay detection, the test trip having a detection zone and a blank zone, comprises:

a processor; and a photoelectric detection circuit, configured to detect signals of the strength of light reflection in the detection zone and the blank zone and feedback detection information to the processor; wherein the photoelectric detection circuit comprises:

at least two light sources, corresponding to positions of the detection zone and the blank zone of the test strip, and able to emit lights corresponding to the detection zone and blank zone of the test strip; and at least one optical detector, configured to receive reflected lights from the detection zone and the blank zone;

wherein the lights emitted by the at least two light sources irradiate the detection zone and blank zone of the strip and are reflected therefrom, and then received by the optical detector, which in turn feedback the detection information to the processor.

With the analyzing and reading device, an optimal optical circuit path between the light sources and the optical detector is provided. The optical path is short, the structure of the device is simple, relatively stronger signals can be retained, no light compensation need to be done, and by the set of the processor, the obtained signals of light strength are transformed into discriminant values for determining and comparing.

In theory, the analyzing and reading device disclosed by the present invention may comprises any number of light sources and any number of optical detectors. For instance, in one embodiment, there may be three light sources, each of them irradiates a corresponding zone of the test strip, three zones may share a common detector, and the detection order is in accordance with the order of light emission of the sources.

In a preferred embodiment, the analyzing and reading device may include a shared optical detector. According to the same principle, the number of the optical detectors may be increased or decreased based on specific test needs.

Preferably, the light sources may be light-emitting diodes, and the optical detector may be a photoelectric sensor.

Preferably, the analyzing and reading device may adopt two light sources, i.e. a first light source and a second light source, wherein the lights emitted by the two sources irradiate the detection zone and blank zone of the test strip, and then are received by the photoelectric sensor after reflection. Preferably, the first and second light sources may be all light-emitting diodes. The first and second light sources separately irradiate the corresponding detection zone and blank zone respectively, wherein the two light sources emit lights successively, and then the reflected lights are received by the common photoelectric sensor; thus, the structure is simpler, the interference is less, and the detection results are more accurate.

Preferably, the first and second light sources may be all green light-emission diodes (green LED), and under the condition of the assay reaction, the emitted lights irradiate the colored detection zone and the blank zone respectively, then a relatively larger contrast of reflection effect is obtained, which increases the accuracy of the readings, especially when the detection zone after reaction is red.

Preferably, the wavelengths of the first and second light sources may be the same.

Preferably, the at least two light sources may emit lights at different times, while the photoelectric sensor receives reflected lights from different zones also at different times.

Preferably, when the analyzing and reading device includes a plurality of light sources, these light sources are optimally set, such that each light source only irradiates a specific zone, and there is a diaphragm between the light sources and between the light sources and the optical detector, so as to restrict the influences among the strip zones irradiated by each of the light sources and among the light sources, and eliminate the impact of the detected lights.

Preferably, the analyzing and reading device may further comprise a T-shaped diaphragm which separates the first, second light sources and the photoelectric sensor from one another, so as to avoid light interferences between the blank zone and the detection zone and between a light-emitting zone and a light-receiving zone.

The two light sources and the photoelectric sensor locate on one side opposite to the detection zone and blank zone, wherein the two light sources are in the same column, while the photoelectric receiver locates opposite to the two sources, and a T-shaped diaphragm is provided between the sources and the sensor, so as to prevent the interference between lights with same or different wavelengths from different light sources. This arrangement makes that, when in the use, lights from different light sources may successively irradiate the detection zone and the blank zone respectively, and the photoelectric sensor successively receives lights diffusely reflected from different light sources. The photoelectric sensor generates a voltage in a positive linear correlation with the strength of the light irradiated thereon. The voltage is caused by the accumulation of the marker, and at the same time, it is also dependent on the amount of the assay substance contained in the sample; then, after detecting the amount existed in the sample, the processor calculates a discriminant value based on the calculation principle of discriminant value, and compares the value with a threshold. The reflected lights may be measured by the photoelectric sensor, wherein the reflected lights refer to lights entered into the optical detector (photoelectric sensor) after the lights from the light sources being reflected by the test strip.

The humidity of the test strip will be various with the passage of time. In the present invention, after detecting the strength of light, the discriminant value is calculated by setting a calculation formula, and then compared with changing threshold, so as to achieve an optimal discriminant result.

In the above arrangement, preferably, the light sources are light-emitting diodes, and preferably the optical detector is a photoelectric sensor; a processor is provided for transforming a light-strength signal into a discriminant value that can be compared.

Preferably, there is a gap between the T-shaped diaphragm, which locates among the first light source, the second light source and the photoelectric sensor, and the detection zone and blank zone of the test strip. Lights emitted by the first and second light sources irradiate the detection and blank zones of the test strip, and then the reflected lights enter the photoelectric sensor through the gap and are received by the sensor. The photoelectric sensor and the light sources are located on the same side. The reflected lights mainly are those lights diffusely reflected through the gap of the diaphragm among the light sources and the photoelectric receiver.

Signals accumulated during the detection procedure include the forming or accumulating of materials easily to be detected (e.g. the result of color reaction). Specifically, the assay preferably includes the accumulation of a marker, usually the accumulation of the marker in the detection zone. The marker may be colored particles like enzyme, radioisotope tracer, fluorescein, colloidal gold, color latex, etc.

Usually, certain assay substance in the sample may cause the accumulation of the signals; however, in some cases, for example, in a competitive reaction, the assay substance will not cause the accumulation of the related signals. The reaction that causes the accumulation of signals may be any suitable reaction, such as conventional chemical reaction between two chemical entities, enzyme-linked reaction, or immunoconjugation reaction. The preferable immunoconjugation reaction will include at least one conjugation of biological molecules.

The preferable reactions include the conjugation of the marker composite body with the specific reagent of the test strip fixed on the detection zone, and the marker accumulates in the conjugation area.

Usually, the blank control zone only serves as an area of "background" signal, for example, such signal can be used for calibrating the analyzing and reading device and/or provide a referable background signal.

Preferably, the test strip comprises a porous, water permeable carrier, which includes a specific conjugation reagent with marker and a specific conjugation reagent without marker.

The analyzing and reading device detects the accumulation amount of the marker, wherein the detection signal is proportional to the accumulation amount of the marker, and according to the calculation formula of discriminant value, the discriminant value is also proportional to the accumulation amount of the marker. The analyzing and reading device can measure optical properties, such as the amount of reflected lights in the detection zone or the blank zone. The reflected lights mean the lights reflected from the porous, water-permeable carrier or other liquid-delivering means to the photoelectric sensor.

Preferably, the analyzing and reading device further includes a housing made of opaque (i.e. light-tight) synthetic plastic, which is usually a synthetic plastic material, such as ABS, polystyrene, etc.

Preferably, the housing of the analyzing and reading device has a pore for receiving at least part of the test strip in the internal of the analyzing and reading device; the positions, shapes and sizes of the pore, the light sources and the optical detector are set so that after the installation of the test strip, lights emitted by the light sources incident to the detection zone and the blank zone, and are reflected therefrom to form the reflected lights, which then incident to the photoelectric sensor and make the sensor generate an assay signal representing the amount of the analyte in the zones. The test strip is fixed in the pore, wherein the test strip comprises a sample-sucking bar, wherein a half of the bar exposes outside of the pore, and another half of the bar is inside the housing of the analyzing and reading device; the outside part of the sample-sucking bar is used for sucking the sample liquid, and the detection zone and blank zone provided on the test strip are inside the housing of the analyzing and reading device, opposite to the light sources and the optical detector of the photoelectric detection circuit. The test strip is fixed inside the analyzing and reading device, so as to avoid inaccuracy caused by the movement of the strip, and the strip need not to be re-positioned.

The sample-sucking bar of the test strip may be any conventional test sample-sucking bar of cross-flow type, preferably include a porous, water-permeable carrier, which comprises a specific reagent combined with a marker and a specific conjugation reagent not having marker.

Preferably, the marker may be colored particle.

Preferably, the light source and the optical detector may be configured as not beyond 0.5 cm$^2$, that complies with the demand of volume miniaturization.

The present invention also provides an analyzing and reading method which uses the above-mentioned analyzing and reading device, wherein the method comprises the following steps: the processor respectively controls the respective lightening of the at least two light sources according to a timing design; after irradiating the detection zone and the blank zone of the test strip, the lights are reflected and then received by an optical detector; then the optical detector feedbacks the detection information to the processor; and, the processor makes analysis and decision based on the detection information received.

The timing design of the processor may be implemented by software.

The analyzing and reading device provides an optimal optical path between the light source and the optical detector, and obtains a signal of light strength; the processor is set so that the signal will be transformed into a discriminant value for determining and comparing. Such optical-path-optimizing device and reading method can be used in other similar spectrometric detection equipment.

Compared with the prior art, the present invention has the following advantages:

The analyzing and reading device of the present invention is simple, economical and practical; based on the selected material, the overall cost is relatively low; using the device and method for analysis and reading according to the present invention, there is less interference when reading and a high accuracy will be achieved.

DETAILED DESCRIPTION OF THE PREFERRED EMBODIMENTS

Figure 1:
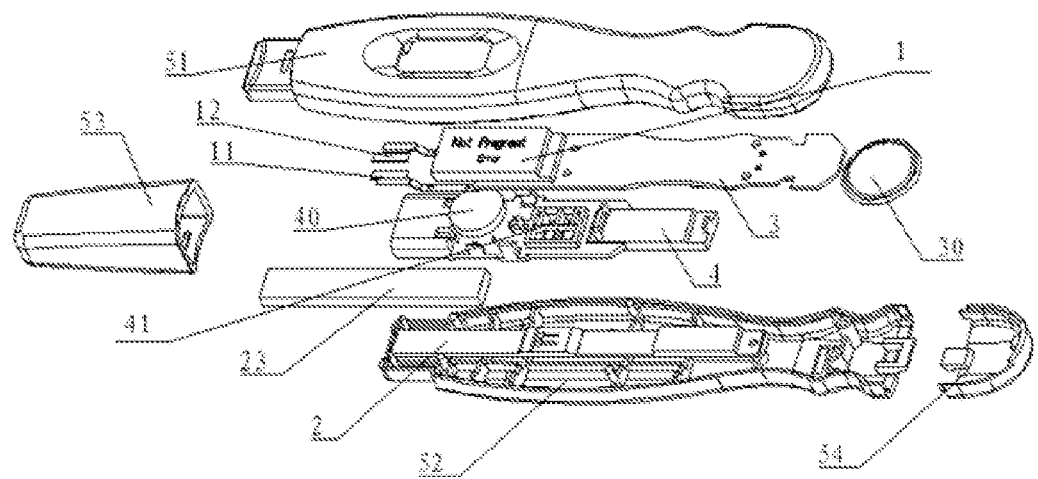
FIG. 1 is an exploded view for showing the structure of the analyzing and reading device according to an embodiment of the present invention.
Figure 2:
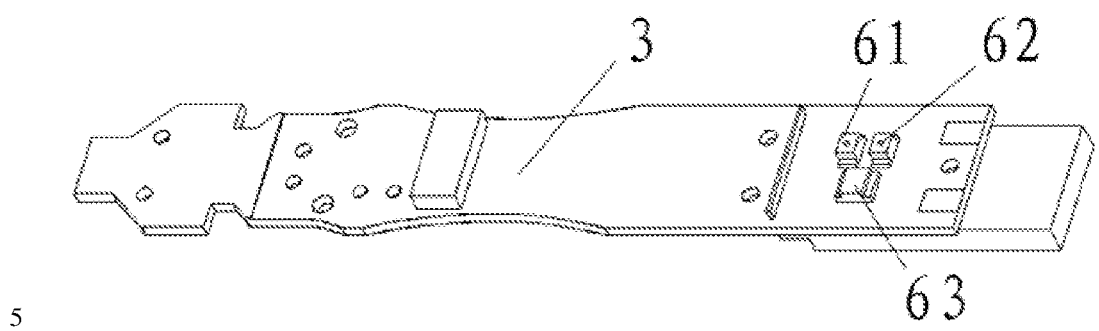
FIG. 2 schematically illustrates the distribution of the light sources and the photoelectric sensor of the analyzing and reading device according to an embodiment of the present invention.
Figure 3:
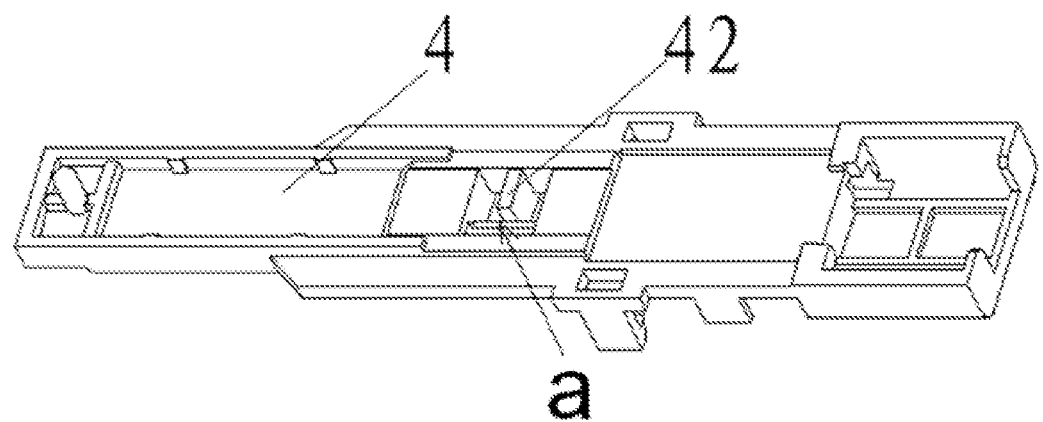
FIG. 3 schematically illustrates the T-shaped diaphragm of the analyzing and reading device according to an embodiment of the present invention.
Figure 4:
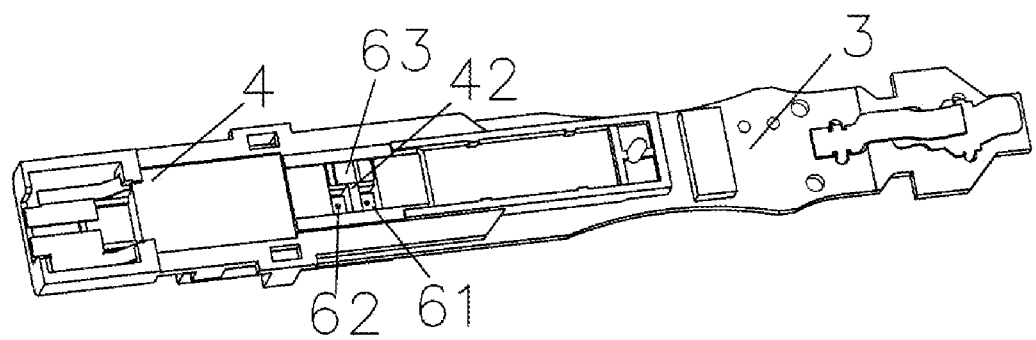
FIG. 4 schematically illustrates the combination of the T-shaped diaphragm with the light sources and the photoelectric sensor of the analyzing and reading device according to an embodiment of the present invention.
Figure 5:
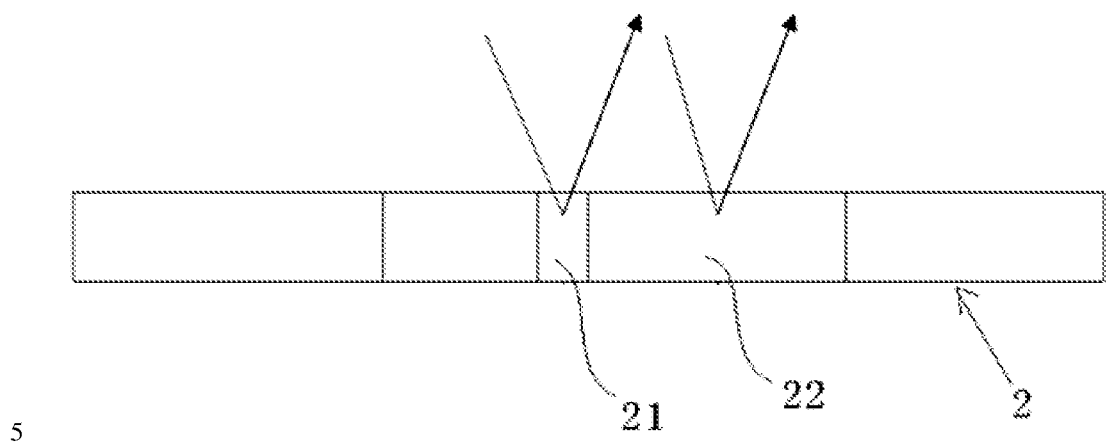
FIG. 5 schematically illustrates the light refection principle in the detection zone and the blank zone of the present invention.

Referring to FIG. 1, in this embodiment, the analyzing and reading device of the present invention specifically includes a processor 1 (CPU) or microcontroller, a test strip 2, a photoelectric detection circuit (not shown), a base board 3, a bracket 4, and a housing. The processor 1 and the photoelectric detection circuit are provided on the base board 3. The strip 2 is provided on one side of the racket 4, while the base board 3 locates on the other side of the racket 4. A detection window 41 is provided in the racket 4. A detection zone and a blank zone are provided on the test strip 2. The photoelectric detection circuit and the detection, blank zones locate respectively on both sides of the detection window 41 and corresponding to each other. The photoelectric detection circuit comprises two LEDs (served as light sources) and a photoelectric sensor; wherein lights emitted by the two LEDs respectively irradiate the detection zone and the blank zone through the detection window 41, and after being reflected, the lights are received by the photoelectric sensor; the processor is configured to detect the output of the photoelectric sensor, so as to determine the accumulation amount of the signal, then calculate a discriminant value, and finally compare the discriminant value with a threshold.

Desiccant 40 is provided on the racket 4 in order to keep the drying in the device, and to guarantee the accuracy of the detection.

In this embodiment, the electric power source used in the analyzing and reading device is a 3V button battery 30. In this embodiment, the housing includes an upper housing 51, a lower housing 52, a front cover 53 and a battery cover 54. The processor 1, the test strip 2, the photoelectric detection circuit, the base board 3 and the racket 4 are placed in the housing. The battery cover 54 can be separately opened to replace the battery. In a preferred embodiment, the housing is about 15 cm in length, about 2.5 cm in width, about 1.5 cm in height, and made of light-tight material, usually of synthetic plastic material (such as ABS, polystyrene, etc.).

Referring to FIGS. 2-5, the photoelectric detection circuit comprises two green LEDs 61, 62 (respectively served as the first, second light sources) and a photoelectric sensor 63, wherein the emitted lights irradiate the detection zone 21 and the blank zone 22 of the test strip 2, and after being reflected, the lights are received by the photoelectric sensor 63. The light sources and the photoelectric sensor are configured to not exceed 0.5 cm$^2$, which complies with the demand of volume miniaturization.

The two LEDs 61, 62 and the photoelectric sensor 63 are separated to one another by a T-shaped diaphragm 42 positioned in the detection window 41, so as to prevent light interference between the blank zone 21 and the detection zone 22, and between light-emitting zone and light-receiving zone. On one side of the detection window 41 there are the two LEDs 61, 62 and the photoelectric sensor 63, while on the other side there are the blank zone 21 and the detection zone 22. The two light sources are in a same column, and the photoelectric receiver locates opposite to the two light sources; they are separated by the T-shaped diaphragm, so as to prevent light interference between the lights of the two deferent light sources, wherein the lights have same or different wavelengths.

The head a of the T-shaped diaphragm 42 is slightly lower than the other part of the diaphragm, so as to form a gap between the diaphragm 42 and the test strip 2. The two LEDs 61, 62 respectively and separately correspond to the detection zone 21 and the blank zone 22. The two light sources successively emit lights which irradiate the detection zone 21 and the blank zone 22 and are then reflected. The reflected lights are received by the common photoelectric sensor 63 through a gap between the T-shaped diaphragm 42 and the test strip 2; the photoelectric sensor and the light sources are positioned at the same side. The reflected lights mainly are the lights diffusely reflected via the gap of the diaphragm among the light sources and the photoelectric receiver. Such structure is simpler, and has less interference and more accurate detection result.

A pore (not shown), which can be covered by a front cover 53, is provided in the front end of the housing of the analyzing and reading device. The test strip 2 is fixed in the pore; the test strip comprises a sample-sucking bar 23. A half of the bar is exposed outside the pore and the other half of the bar is positioned inside the housing of the analyzing and reading device. The outside part of the sample-sucking bar 23 is used for sucking sample liquid. The detection zone 21 and the blank zone 22 provided on the test strip are positioned inside the housing of the device, opposite to the light sources and the optical detector of the photoelectric detection circuit. The test strip 2 is fixed in the analyzing and reading device, particularly fixed on the racket 4, to avoid inaccuracy caused by the movement of the test strip, and the test strip need not to be re-positioned.

The sample-sucking bar 23 of the test strip may be any conventional cross-flow test sample-sucking bar, preferably comprises a porous, water-permeable carrier, which includes a specific conjugation reagent having marker and a specific conjugation reagent not having marker. The analyzing and reading device detects the accumulation amount of the marker, wherein the detection signal is proportional to the accumulation amount of the marker, and according to the calculation formula of discriminant value, the discriminant value is also proportional to the accumulation amount of the marker. The analyzing and reading device can measure optical properties, such as the amount of the reflected lights in the detection zone or the blank zone. The reflected lights mean the lights reflected from the porous, water-permeable carrier or other liquid-delivering means to the photoelectric sensor.

The marker is colored particles, which may be enzyme, radioisotope tracer, fluorescein, colloidal gold, color latex, etc.

As a preferred embodiment, a liquid crystal display connected to the processor for outputting the working condition and determination result of the analyzing and reading device is provided on the upper housing 51 of the device.

Figure 6:
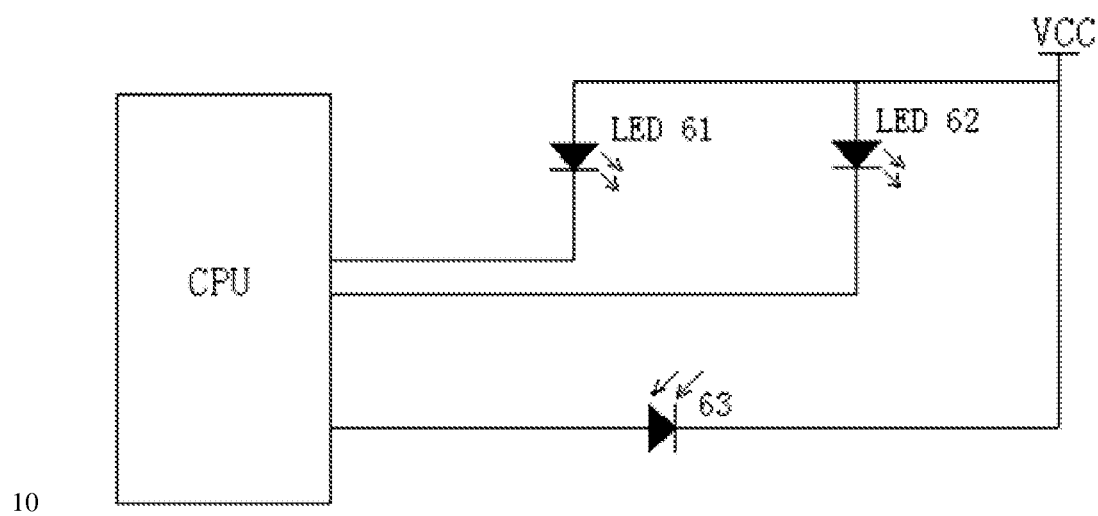
FIG. 6 schematically illustrates the structure of the photoelectric detection circuit according to an embodiment of the present invention.
Figure 7:
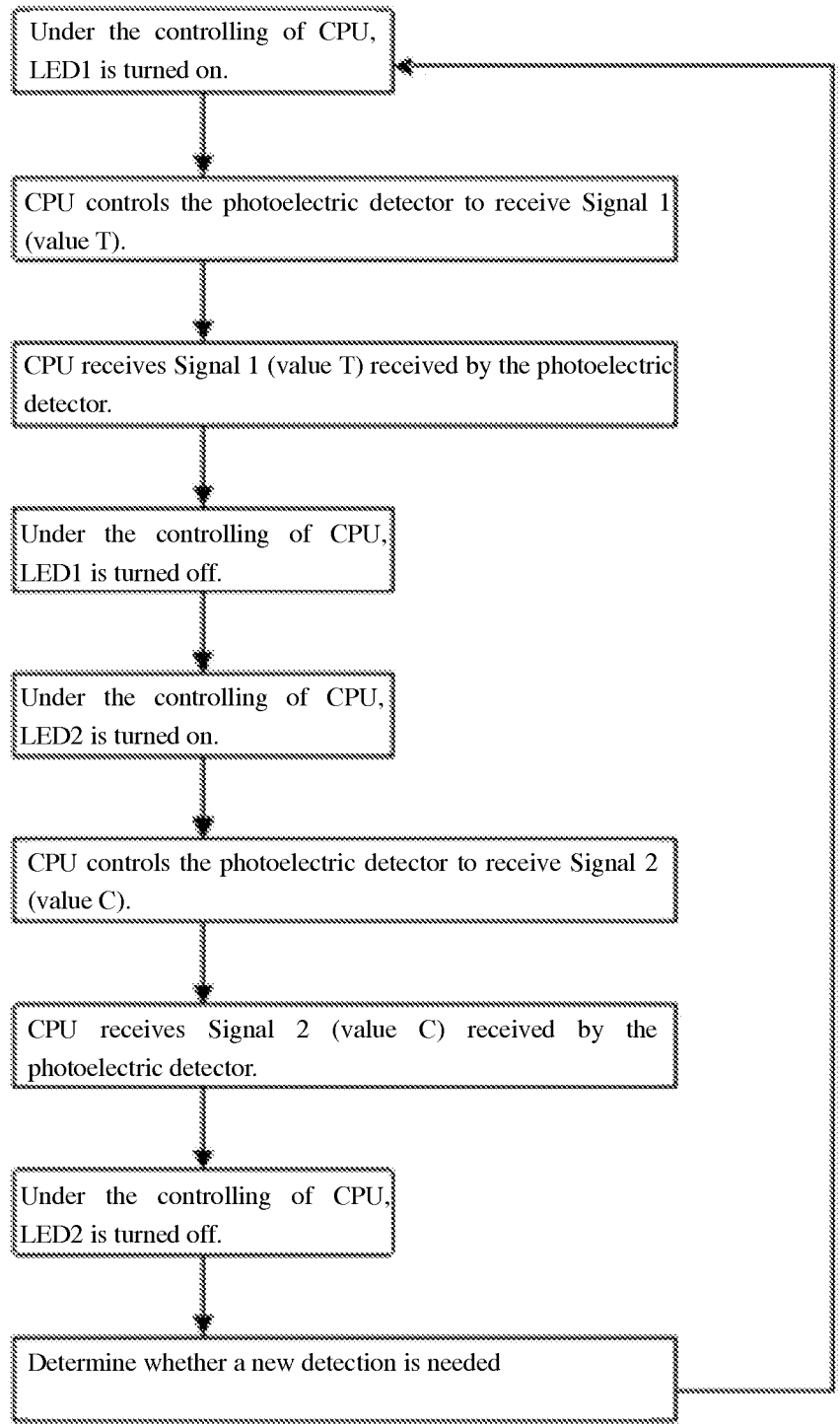
FIG. 7 is a schematic flow diagram of the analyzing and reading method according to an embodiment of the present invention.

Referring both to FIGS. 6 and 7, the two LEDs 61, 62 successively emit lights at different times, and this is realized by programming the processor. Also, the photoelectric sensor receives the reflected lights from different zones at different times. Such arrangement makes that, when in use, the lights from different light sources may successively and respectively irradiate the detection zone and the blank zone, and the photoelectric sensor also successively receives the diffusely reflected lights from the different light sources. The photoelectric sensor generates a voltage in a positive linear correlation with the strength of the light irradiated thereon. The voltage is caused by the accumulation of the marker, and at the same time, it is also dependent on the amount of the analyte contained in the sample; then, after detecting the amount existed in the sample, the processor calculates a discriminant value based on the calculation principle of discriminant value, and compares the value with a threshold. The reflected lights may be measured by the photoelectric sensor, wherein the reflected lights refer to the lights entered into the photoelectric sensor after the lights from the light sources being reflected by the test strip.

The present invention also provides a analyzing and reading method which uses the above-mentioned analyzing and reading device; Referring to FIG. 7, the method comprises the following steps: the processor controls the lighting of at least two light sources respectively according to a timing design; after irradiating the detection zone and the blank zone of the test strip, lights are reflected and then received by an optical detector; the optical detector feedbacks the detection information to the processor; the processor makes analysis and decision based on the detection information received.

The timing design of the processor may be realized by software.

Usually, certain analyte in the sample may cause the accumulation of the signals; however, in some cases, for example, in a competition reaction, the certain analyte will not cause the accumulation of the related signals. The reaction that causes the accumulation of signals may be any suitable reaction, such as conventional chemical reaction between two chemical entities, enzyme-linked reaction, or immunoconjugation reaction. The preferable immunoconjugation reaction will include at least one conjugation of biological molecules.

After leaving the factory, the device is in a dormant state in order to reduce energy consumption; only when the sample has been sucked by the test sample-sucking bar, and the flow of the sample liquid in the sample-sucking bar induces the change of the electrical resistance of the circuit, the device will be automatically activated from the "dormant" state to a working state.

In use, the front end of the sample-sucking bar is directly inserted into the sample; after the addition of the sample, the device will be activated; then, a left electrode 11 and a right electrode 12 of the photoelectric detection circuit are conductively connected, so as to turn on the device and start a normal measurement; after waiting 8 seconds, the device enters the work mode, this time, the two LEDs successively emit lights, and the reader starts to operate; corresponding voltages are detected by the photoelectric sensor and sent to the processor; the signals detected at this moment are initial values of the detection zone and the blank zone, which are used as reference signals before sample addition. After waiting N seconds, the detection operation is repeated, and the signals detected at this moment are served as result determining signals, which are then combined with corresponding algorithm to achieve detection results; wherein the algorithm can be referred to general operations in the art and is not described here. The light-strength signals are received according to the chronological order of the lightening of the light sources. The initial values are scanned in order to use them as the background ones for calculating discriminant values.

During operation, the sample can also be directly poured on the sample-sucking bar; the pouring should be done carefully to not get the other parts wet; the device is taken out and placed in a flat position with the liquid crystal display facing up when a funnel-shaped symbol displayed on the observing window starts to flash (at the same time, a buzzer starts to ring); or, the sample is collected into a clean, single-use container or clean container, and then the sample-sucking bar of the detection pen is inserted into the sample with at least three-fourths of the bar being immerged below the liquid level of the sample; the detection pen of the device is taken out and placed in a flat position with the liquid crystal display facing up when the funnel-shaped symbol displayed on the observing window starts to flash (at the same time, a buzzer starts to ring). According to a pre-set procedure, the device starts to measure one or more values for conducting the comparing.

The analyzing and reading device provides an optimal optical path between the light source and the optical detector, and obtains a signal of light strength; the processor is set so that the signal will be transformed into a discriminant value for determining and comparing. Such optical-path-optimizing device and reading method can be used in other similar spectrometric detection equipment.

The above mentioned relates only to preferred embodiments of the present invention, which do not limit the protection scope of the present invention. All equivalent transformations based on the technical solutions of the present invention belong to the protection scope of the present invention.

What is claimed is:

1. An analyzing and reading device, for reading and analyzing a test strip for assay detection, the test trip having a detection zone and a blank zone, comprising:
    a processor;
    a photoelectric detection circuit, configured to detect signals of the strength of light reflection in the detection zone and the blank zone and feedback detection information to the processor; wherein the photoelectric detection circuit comprises:
    at least two light sources including a first light source and a second light source, corresponding to positions of the detection zone and the blank zone of the test strip, and able to emit lights corresponding to the detection zone and blank zone of the test strip; and
    at least one optical detector, configured to receive reflected lights from the detection zone and the blank zone;
    wherein the lights emitted by the at least two light sources irradiate the detection zone and blank zone of the strip and are reflected therefrom, and then received by the optical detector, which in turn feedback the detection information to the processor;
    a diaphragm separating the first light source from the second light source and the at least one optical detector from the at least two light sources; and
    a gap formed between the diaphragm and the test strip.

2. The analyzing and reading device according to claim 1, wherein the optical detector is a photoelectric sensor.

3. The analyzing and reading device according to claim 2, wherein the lights emitted by the two light sources irradiate the detection zone and blank zone of the test strip, and then are received by the photoelectric sensor after reflection.

4. The analyzing and reading device according to claim 3, wherein both the first and second light sources are light emitting diodes.

5. The analyzing and reading device according to claim 4, wherein both the first and second light sources are green light emitting diodes.

6. The analyzing and reading device according to claim 5, wherein wavelengths of the first and second light sources are the same.

7. The analyzing and reading device according to claim 1, wherein the processor is configured to emit light from the at least two light sources at different times.

8. The analyzing and reading device according to claim 3, wherein the diaphragm is a T-shaped diaphragm.

9. The analyzing and reading device according to claim 8, wherein the gap is formed between the T-shaped diaphragm among the first light source, the second light source and the photoelectric sensor, and the detection zone and blank zone of the test strip; the lights emitted by the first and second light sources irradiate the detection and blank zones of the test strip, and then the reflected lights enter the photoelectric sensor through the gap and are received by the sensor.

10. The analyzing and reading device according to claim 1, wherein the device further comprises a housing made of light-tight synthetic plastic.

11. The analyzing and reading device according to claim 1, wherein the test strip comprises a porous water permeable carrier, which comprises a specific conjugation reagent with marker and a specific conjugation reagent without marker.

12. The analyzing and reading device according to claim 11, wherein the marker is colored particles.

13. An analyzing and reading method by using the analyzing and reading device according to claim 1, comprising the following steps: controlling by the processor the respective lightening of the at least two light sources according to a timing design to irradiate the detection zone and the blank zone of the test strip; receiving by the optical detector lights reflected; then feeding back by the optical detector detection information to the processor; and, making analysis and determination by the processor according to the detection information received.

14. The analyzing and reading device according to claim 1, wherein the processor is configured to:
    receive the detection information from the optical detector;
    determine an accumulation amount of a marker based on the detection information;
    calculate a discriminant value based on the accumulation amount of the marker; and
    compare the discriminant value with a threshold.

* * * * *